United States Patent [19]
Naylor et al.

[11] Patent Number: 5,871,980
[45] Date of Patent: Feb. 16, 1999

[54] PROCESS FOR THE MICROBIOLOGICAL PRODUCTION OF PHA-POLYMERS

[75] Inventors: Linda Anne Naylor, Eaglescliffe; John Christopher Wood, Peterlee, both of United Kingdom

[73] Assignee: Monsanto Company, St. Louis, Mo.

[21] Appl. No.: 894,347

[22] PCT Filed: Feb. 9, 1996

[86] PCT No.: PCT/GB96/00293

§ 371 Date: Dec. 1, 1997

§ 102(e) Date: Dec. 1, 1997

[87] PCT Pub. No.: WO96/25509

PCT Pub. Date: Aug. 22, 1996

[30] Foreign Application Priority Data

Feb. 17, 1995 [GB] United Kingdom ............. 9503174

[51] Int. Cl.⁶ .................. C12P 7/62; C12P 7/64; C12P 1/05; C08G 63/06
[52] U.S. Cl. ........... 435/135; 435/134; 435/829; 528/361
[58] Field of Search ................... 435/134, 135, 435/829; 528/361

[56] References Cited

U.S. PATENT DOCUMENTS 5,346,817  9/1994  Akiyama et al. ............... 435/135

FOREIGN PATENT DOCUMENTS 0 520 405  12/1992  European Pat. Off. ......... C12P 7/62

OTHER PUBLICATIONS

Database WPI, Week 9043, Derwent Publications Ltd., London, GB; AN 90–325620, XP002003618, "Preparation of polyester biopolymer—containing units of 3–and 4–hydroxy–butyrate obtained by culturing bacterial strain of alcaligenes," & JP 02 234 683 (Mitsubishi Kasei Corp), 17 Sep. 1990.

Appl. Microbiol. Biotechnol., vol. 31, 1989, pp. 168–175, XP002003615, Steinbüchel al. und Schlegel H.G.: "Excretion of pyruvate by mutants of *Alcaligenes eutrophus.*"

Industrial Crops and Products, No. 1, 1993, pp. 157–163, XP002003616, Eggink G., et al., "Oleic acid as a substrate for poly–3–hydroxyalkanoateformation in *Alcaligenes eutrophus* and *asputida.*"

J. Ferm. Bioeng., vol. 74, No. 5, 1992, pp. 288–291, XP002003617, Kenji Tanaka, ET AL. : "Aaccumulation of Polyphosphate and Substrate Gas Utilization Efficiency in PHB Accumlation Phase of Autrophic Batch Culture of *Alcaligenes eutrophus* ATCC17697."

*Primary Examiner*—Herbert J. Lilling
*Attorney, Agent, or Firm*—Gary M. Bond; Arnold, White & Durkee

[57] ABSTRACT

A process for producing poly-3-hydroxyalkanoate (PHA) by culturing Alcaligenes on a low water-solubility aliphatic carboxylic acid and, or hydrolysable derivative of low solubility in pure water, by fermenting the organism in a growth step on a nutrient medium containing inter alia phosphorus in a quantity corresponding to the intended quantity of bacterial cells to be grown until cell growth stops or slows substantially, then in a PHA accumulation stage fermenting the grown cells by feeding said low-solubility carbon source while monitoring pH and adjusting it by addition of ammonia and/or alkaline alkali metal compound until a design quantity of PHA has been produced, and recovering PHA from the product. Further phosphorus may be fed to the accumulation stage at a rate sufficient to permit some bacterial growth but insufficient to permit growth to the exclusion of PHA accumulation. The over-all carbon (as C) to phosphorus (as P) weight ratio is typically in the range 40–100 in the growth stage and 300 to 600 in the accumulation stage.

30 Claims, No Drawings

PROCESS FOR THE MICROBIOLOGICAL PRODUCTION OF PHA-POLYMERS

THIS INVENTION relates to polymer production and in particular to a process for microbiologically producing poly-3-hydroxyalkanoate (PHA) from a fatty carbon source.

According to EP-A-520405 such a PHA containing 3-hydroxybutyrate (HB) repeating units can be made by culturing, possibly under nitrogen and phosphorus limitation, a strain belonging to the genus *Alcaligenes lipolytica* (FERM BP-3819) on a $C_{10}$–$C_{22}$ fatty acid or derivative thereof; however, other Alcaligenes (specifically *A. eutrophus* and *A. latus*) are reported to be incapable of growth on such feedstock, or at best capable of only extremely slow growth.

According to Eggink et al (Industrial Crops and Products 1993, 1, 157–163) such PHA can be made by culturing *A. eutrophus* on oleic acid, the yield of PHA being greater under nitrogen limitation.

We have now discovered fermentation conditions in which Alcaligenes will produce PHA at high yields and/or output rates from aliphatic carboxylic acid or derivatives hydrolysable thereto as carbon source.

According to the invention a process for producing PHA comprises culturing at least one strain of Alcaligenes on a carbon source comprising at least one aliphatic carboxylic acid and/or derivative thereof hydrolysable thereto said acid or derivative or mixture thereof being of low solubility in pure water, by the steps of:

(a) providing a body of nutrient medium containing assimilable compounds of nitrogen, phosphorus, sulphur and trace elements, the phosphorus quantity corresponding to the requirement of the intended quantity of bacterial cells to be grown;
(b) inoculating the body with viable cells of Alcaligenes;
(c) providing in said body a quantity of assimilable carbon compound at least corresponding to the quantity of bacterial cells to be grown;
(d) aerobically fermenting the inoculated body while monitoring pH and adjusting it by addition of ammonia and/or alkaline alkali metal compound until cell growth stops or slows substantially;
(e) aerobically fermenting the product of step (d) by feeding said low-solubility carbon source while monitoring pH and adjusting it by addition of ammonia and/or alkaline alkali metal compound, until a design quantity of PHA has been produced; and
(f) recovering PHA from the product of step (e).

The carbon compound provided in step (c) can be any that the Alcaligenes can assimilate. Thus it can be for example a sugar, a sugar alcohol, a sugar acid or an alkanol or alkanoic acid. Conveniently it is an aliphatic acid or derivative hydrolysable thereto, for example, the same as is to be used in step (e).

In step (d) cell growth stops or slows substantially when the phosphorus provided in step (a) has been exhausted, typically to less than 10 mg P per liter of supernatant. The assimilable carbon compound is normally fed gradually so as to avoid exceeding the provision of oxygen for the aerobic fermentation and (where appropriate) to avoid a toxic concentration of such compound. The over-all carbon (as C) to phosphorus (as P) weight ratio in this step is typically in the range 40–100, especially 50–80, differing according to the chemical composition of the compound.

In step (e) and possibly step (c) the aliphatic acid whether used as such or as a hydrolysable derivative, is preferably less than 3; especially less than 1,% w/w soluble in pure water at ambient temperature. Typically it contains one or more alkyl groups containing 8–25, especially 10–22 carbon atoms. Preferably the derivative is an ester, conveniently a triglyceride, especially a naturally occurring triglyceride. The fatty acid may be saturated (provided this does not lead to a melting point higher than the temperature of steps (d) and (e)) or mono- or poly-unsaturated. Examples of triglycerides are animal products such as butter, whale oil, beef tallow, pork fat, mutton fat; fish oils; and vegetable oils such as olive oil, corn oil, rapeseed oil, castor oil, sunflower oil and linseed oil. As-extracted unsaturated oils can be partly or wholly hydrogenated. It appears that such triglycerides need not be refined to human food standard: among the impurities tolerated or productively assimilated are the corresponding free acids, phospholipids and traces of coloured materials such as trace metal compounds and chlorophyll. As alternative or additional ester there may be used mono- or di-glycerides, or mono-ester derivatives of the fatty acids such as the methyl esters proposed for use as "bio-diesel". A mixture of derivatives can be used, especially if the carbon source includes material melting at above fermentation temperature.

If the aliphatic acid contains an even number of carbon atoms and is the sole carbon source in step (e) the product PHA is substantially or wholly polyhydroxybutyrate (PHB) homopolymer. If polyhydroxybutyrate/valerate copolymer (PHBV) is required, there should be present a carbon source containing an odd number of carbon atoms; this may be part or all of the aliphatic acid (derivative) or may be additional thereto, for example propionic acid or n-propyl alcohol. The product PHA preferably contains up to 30 mol % of V, especially 3–25 mol % V, balance B.

The process can use any species or strain of Alcaligenes. Specific examples are *A. eutrophus, A. latus, A. faecalis, A. ruhlandii, A. aquamarinus, A. lipolytica*. It is an especial advantage of the process that bacteria other than *A. lipolytica* appear to be at least as active and efficient as *A. lipolytica*, which was until this invention believed to be uniquely capable of converting fatty acid esters to PHA.

The cell dry-weight at the end of step (e) or in the steady state of that step if operating continuously is preferably in the range 100–400 g/liter. The design quantity of PHA preferably corresponds to a PHA content in the range 60–80% w/w on cell dry weight (including PHA).

In a preferred form of the process phosphorus is fed to step (e) at a rate sufficient to permit some bacterial growth but insufficient to permit maximum growth, that is, growth to the exclusion of PHA accumulation or growth to the maximum available extent alongside accumulation. (The latter applies to those species of Alcaligenes capable of simultaneous growth and accumulation). Typically the weight ratio of total carbon (as C) to total phosphorus (as P) fed to step (c) is in the range 300 to 600. This appears to give a high output of PHA in a fed batch fermentation in virtue not only of the increased number of PHA-bearing cells and of the high PHA content of the cells, but also of faster reaction and high propionate efficiency. The phosphorus feed, conveniently as phosphate, is at a steady rate during the fermentation and preferably is at a fixed proportion of the carbon feed.

For step (e) the feeds, in addition to carbon source and (if any) said phosphorus compound, may include also other essential nutrients such as nitrogen, sulphur and trace elements, supplementing those present after step (d).

Step (e), and also step (d) if an oily carbon source of low water solubility is used, are carried out preferably with vigorous agitation at least by air-sparging and possibly also mechanically, so as to maximise the active surface area of the oil.

The pH in the growth (d) and accumulation (e) steps is preferably kept within half a pH unit of the value for most rapid reaction. Typically the pH is between 6.0 and 7.5, measured in the broth at fermentation temperature. Conveniently the addition of aqueous ammonia or the alkaline alkali metal compound is effected automatically in response to pH measurement by glass electrode.

The temperature in steps (d) and (e) can be as normally used for Alcaligenes using water-soluble carbon sources, for example in the range 20°–40° C., especially 28°–38° C.

The product PHA is R-stereospecific and typically consists of 3-hydroxybutyrate repeating units alone ("PHB") or with 3-hydroxyvalerate units ("PHBV"), present at up to 30, especially 3–25, mol percent. The molecular weight of the PHA is for example over 50000, especially over 100000, and up to eg $2 \times 10^6$.

Recovery of PHA in step (f) can be by any convenient method. In one general method the PHA-bearing cells are separated from the fermentation liquid by centrifugation, the cells are broken mechanically or chemically and the PHA is extracted in a solvent such as a halogenated hydrocarbon or an alkylene carbonate. In another the non-PHA cell material is solubilised by some or all of mechanical action, heat-shock, enzyme attack, surfactant attack and oxidation, leaving PHA particles as laid down in the cells or agglomerates of such particles. Such particles or agglomerates may be recovered dry, for use in melt-processing or solvent-processing, or as a latex for use as a coating or adhesive or for later conversion to dry PHA.

The following Examples show the production of PHBVs having a similar V content (ranges 6.9–8.7 mol %)

EXAMPLE 1

A stirred air-sparged laboratory fermenter of 15 liters capacity was charged with 8 liters of a medium containing per liter the following components:

| | |
|---|---|
| 3.00 g | Rape Seed Oil |
| 0.93 ml | Conc $H_3PO_4$ (400 mg/l P) |
| 2.18 g | $MgSO_4.7H_2O$ |
| 1.81 g | $(NH_4)_2SO_4$ |
| 2.18 g | $K_2SO_4$ |
| 0.36 g | Ca acetate |
| 0.14 g | $FeSO_4.7H_2O$ |
| 0.09 g | $Na_2SO_4$ |
| 0.04 g | $MnSO_4.H_2O$ |
| 0.09 g | $ZnSO_4.7H_2O$ |
| 4.50 mg | $CuSO_4.5H_2O$ |

The pH was controlled at 6.8 by addition of 7M $NH_4OH$ and the temperature at 34° C.

200 ml (0.2 g of viable cells) of a culture of *Alcaligenes eutrophus* (NCIMB 40124) were then stirred in. The air flow rate was adjusted to maintain a dissolved oxygen tension above 10% of air saturation at 1 bar pressure absolute. Further rape seed oil was fed to achieve an average oil uptake rate of up to 0.13 g per g of non-PHA cell mass per hour.

After 20 h it was noted that the rate of oil uptake decreased substantially, marking the substantial exhaustion of phosphorus. At this point the weight ratio of total carbon fed (as c) to total phosphorus fed (as P) was 60. Thereafter rape seed oil and propionic acid were fed until the uptake rate of those carbon sources became slow, showing that further conversion to PHA was not longer practical.

The resulting biomass was sampled and analysed for cell dry weight, PHA content and PHA valerate content.

EXAMPLE 2

The procedure of Example 1 was repeated with the modification that phosphoric acid was fed with the oil to the fermenter during the PHA accumulation step to the extent of 17% of total phosphorus used, keeping the C/P ratio in the range 400–600 throughout, which was sufficient to increase the cell dry weight to the desired level, but insufficient to effect substantial growth with suppression of PHA accumulation.

EXAMPLE 3

The procedure of Example 1 was repeated with the modification using crude corn oil as carbon source.

Results

The final cell dry weights, yields of PHA and PHA molecular weights obtained in typical runs are shown in the Table.

| Example V mol % | Final Cell Dry Weight g/l | % PHA in Dry Cells | g PHA per g Oil used | PHA Mass (g) | Run Time h | Propionate efficiency mol % |
|---|---|---|---|---|---|---|
| 17.4 | 140 | 64 | 0.63 | 1038 | 80 | 11.2 |
| 28.7 | 204 | 67 | 0.63 | 1728 | 65 | 18.2 |
| 36.9 | 162 | 72 | 0.69 | 1289 | 65 | 24.0 |

It is evident that *Alcaligenes eutrophus* grows actively and accumulates PHA efficiently using rape seed oil or corn oil as carbon source. The phosphate feed during PHA accumulation usefully increases the rate of production of PHA and the efficiency with which propionic acid is converted to valerate repeating units in the PHA. Use of crude corn oil affords a further improvement in propionate efficiency.

We claim:

1. A process for producing poly-3-hydroxyalkanoate (PHA) which comprises culturing at least one strain of Alcaligenes other than *Alcaligenes lipolytica* on a carbon source comprising at least one aliphatic carboxylic acid and/or derivative thereof hydrolysable thereto, said acid or derivative or mixture thereof being of low solubility in pure water, by the steps of:

(a) providing a body of nutrient medium containing assimilable compounds of nitrogen, phosphorus, sulphur and trace elements, the phosphorus quantity corresponding to the requirement of the intended quantity of bacterial cells to be grown;

(b) inoculating the body with viable cells of Alcaligenes;

(c) providing in said body a quantity of assimilable carbon compound at least corresponding to the quantity of bacterial cells to be grown;

(d) aerobically fermenting the inoculated body while monitoring pH and adjusting it by addition of ammonia and/or alkaline alkali metal compound until cell growth stops or slows substantially;

(e) aerobically fermenting the product of step (d) by feeding said low-solubility carbon source while monitoring pH and adjusting it by addition of ammonia and/or alkaline alkali metal compound, until a design quantity of PHA has been produced; and (f) recovering PHA from the product of step (e).

2. A process according to claim 1 in which the carbon compound provided in step (c) is the same as is to be used in step (e).

3. A process according to claim 1 in which the over-all carbon (as C) to phosphorus (as P) weight ratio in step (d)

is typically in the range 40–100, differing according to the chemical composition of the compound.

4. A process according to claim 1 in which phosphorus is fed to step (e) at a rate sufficient to permit some bacterial growth but insufficient to permit growth to the exclusion of PHA accumulation.

5. A process according to claim 4 in which the weight ratio of total carbon as (C) to total phosphorus (as P) fed to step (e) is in the range 300 to 600.

6. A process according to claim 4 in which the phosphorus feed is at a steady rate during fermentation and at a fixed proportion of the carbon feed.

7. A process according to claim 1 in which step (e), an also step (d) if an oily carbon source of low water solubility is used, are carried out preferably with vigorous agitation at least by air-sparging and possibly also mechanically, so as to maximise the active surface area of the oil.

8. A process according to claim 1 in which the cell dry-weight at the end of step (e) or in the steady state of that step if operating continuously is in the range 100–400 g/liter.

9. A process according to claim 1 in which the design quantity of PHA corresponds to a PHA content in the range of 60–80% w/w on cell dry weight (including PHA).

10. A process according to claim 1 in which, to produce polyhydroxybutyrate/-valerate copolymer (PHBV), there is provided in step (e) a carbon source containing an odd number of carbon atoms as part or all of the aliphatic acid and/or derivative thereof hydrolyzable thereto.

11. A process according to claim 1 in which the Alcaligenes strain is *Alcaligenes eutrophus*.

12. The method of claim 1, wherein the Alcaligenes strain is selected from the group consisting of *Alcaligenes eutrophus, Alcaligenes latus, Alcaligenes faecalis, Alcaligenes ruhlandii* and *Alcaligenes aquamarinus*.

13. A process for producing poly-3-hydroxyalkanoate (PHA) which comprises culturing at least one strain of Alcaligenes on a carbon source comprising at least one aliphatic carboxylic acid and/or derivative thereof hydrolyzable thereto, said acid or derivative or mixture thereof being of low solubility in pure water, by the steps of:
   (a) providing a body of nutrient medium containing assimilable compounds of nitrogen, phosphorus, sulphur and trace elements, the phosphorus quantity corresponding to the requirement of the intended quantity of bacterial cells to be grown;
   (b) inoculating the body with viable cells of Alcaligenes;
   (c) providing in said body a quantity of assimilable carbon compound at least corresponding to the quantity of bacterial cells to be grown;
   (d) aerobically fermenting the inoculated body while monitoring pH and adjusting it by addition of ammonia and/or alkaline alkali metal compound until cell growth stops or slows substantially;
   (e) aerobically fermenting the product of step (d) by feeding said low-solubility carbon source while monitoring pH and adjusting it by addition of ammonia and/or alkaline alkali metal compound, until a design quantity of PHA has been produced, wherein the weight ratio of total carbon as (C) to total phosphorus (as P) fed to step (e) is in the range of about 300 to about 600; and
   (f) recovering PHA from the product of step (e).

14. A process according to claim 13 in which the carbon compound provided in step (c) is the same as is to be used in step (e).

15. A process according to claim 13 in which phosphorus is fed to step (e) at a rate sufficient to permit some bacterial growth but insufficient to permit growth to the exclusion of PHA accumulation.

16. A process according to claim 15 in which the phosphorus feed is at a steady rate during fermentation and at a fixed proportion of the carbon feed.

17. A process according to claim 13 in which step (e), an also step (d) if an oily carbon source of low water solubility is used, are carried out preferably with vigorous agitation at least by air-sparging and possibly also mechanically, so as to maximize the active surface area of the oil.

18. A process according to claim 13 in which the cell dry-weight at the end of step (e) or in the steady state of that step if operating continuously is in the range 100–400 g/liter.

19. A process according to claim 13 in which the design quantity of PHA corresponds to a PHA content in the range of 60–80% w/w on cell dry weight (including PHA).

20. A process according to claim 13 in which, to produce polyhydroxybutyrate/valerate copolymer (PHBV), there is provided in step (e) a carbon source containing an odd number of carbon atoms as part or all of the aliphatic acid and/or derivative thereof hydrolysable thereto.

21. A process according to claim 13 in which the Alcaligenes strain is *Alcaligenes eutrophus*.

22. A process for producing poly-3-hydroxyalkanoate (PHA) which comprises culturing at least one strain of Alcaligenes on a carbon source comprising at least one aliphatic carboxylic acid and/or derivative thereof hydrolyzable thereto, said acid or derivative or mixture thereof being of low solubility in pure water, by the steps of:
   (a) providing a body of nutrient medium containing assimilable compounds of nitrogen, phosphorus, sulphur and trace elements, the phosphorus quantity corresponding to the requirement of the intended quantity of bacterial cells to be grown;
   (b) inoculating the body with viable cells of Alcaligenes;
   (c) providing in said body a quantity of assimilable carbon compound at least corresponding to the quantity of bacterial cells to be grown;
   (d) aerobically fermenting the inoculated body while monitoring pH and adjusting it by addition of ammonia and/or alkaline alkali metal compound until cell growth stops or slows substantially, in which the over-all carbon (as C) to phosphorus (as P) weight ratio in step (d) is in the range of about 40 to about 100;
   (e) aerobically fermenting the product of step (d) by feeding said low-solubility carbon source while monitoring pH and adjusting it by addition of ammonia and/or alkaline alkali metal compound, until a design quantity of PHA has been produced; and
   (f) recovering PHA from the product of step (e).

23. A process according to claim 22 in which the carbon compound provided in step (c) is the same as is to be used in step (e).

24. A process according to claim 22 in which phosphorus is fed to step (e) at a rate sufficient to permit some bacterial growth but insufficient to permit growth to the exclusion of PHA accumulation.

25. A process according to claim 22 in which the phosphorus feed is at a steady rate during fermentation and at a fixed proportion of the carbon feed.

26. A process according to claim 22 in which step (e), an also step (d) if an oily carbon source of low water solubility is used, are carried out preferably with vigorous agitation at least by air-sparging and possibly also mechanically, so as to maximize the active surface area of the oil.

27. A process according to claim 22 in which the cell dry-weight at the end of step (e) or in the steady state of that step if operating continuously is in the range 100–400 g/liter.

28. A process according to claim 22 in which the design quantity of PHA corresponds to a PHA content in the range of 60–80% w/w on cell dry weight (including PHA).

29. A process according to claim 22 in which, to produce polyhydroxybutyrate/valerate copolymer (PHBV), there is provided in step (e) a carbon source containing an odd number of carbon atoms as part or all of the aliphatic acid and/or derivative thereof hydrolyzable thereto.

30. A process according to claim 22 in which the Alcaligenes strain is *Alcaligenes eutrophus*.

* * * * *